US00PP12693P2

(12) United States Plant Patent
Floré

(10) Patent No.: US PP12,693 P2
(45) Date of Patent: Jun. 11, 2002

(54) RHODODENDRON PLANT NAMED 'ANGELINA'

(75) Inventor: Etienne Floré , Lochristi (BE)

(73) Assignee: Hortibreed B. V., Lochristi (BE)

( * ) Notice: Subject to any disclaimer, the term of this patent is extended or adjusted under 35 U.S.C. 154(b) by 0 days.

(21) Appl. No.: 09/778,211

(22) Filed: Feb. 8, 2001

(51) Int. Cl.[7] ..... A01H 5/00
(52) U.S. Cl. ..... Plt./238
(58) Field of Search ..... Plt./238

(56) References Cited

PUBLICATIONS

GTITM UPOVROM Citation for 'Angelina' as per QZ PBR 980754; Jun. 17, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Rhododendron plant named 'Angelina', characterized by its uniform, upright and outwardly spreading plant habit; dark green foliage; numerous showy double hose-in-hose white-colored flowers; and long flowering period.

1 Drawing Sheet

BACKGROUND OF THE INVENTION

The present invention relates to a new and distinct cultivar of Rhododendron, botanically known as *Rhododendron simsii* and hereinafter referred to by the name 'Angelina'.

The new Rhododendron is a product of a planned breeding program conducted by the Inventor in Lochristi, Belgium. The objective of the breeding program is to create new long-flowering Rhododendron cultivars.

The new Rhododendron originated from a cross made by the Inventor in 1990 in Lochristi, Belgium, of two unidentified proprietary seedling selections of *Rhododendron simsii.*

The new Rhododendron was discovered and selected by the Inventor as a flowering plant within the progeny of the stated cross in a controlled environment in Lochristi, Belgium. The selection of this plant was based on its double white flowers.

Asexual reproduction of the new Rhododendron by terminal cuttings taken in a controlled environment in Lochristi, Belgium, has shown that the unique features of this new Rhododendron are stable and reproduced true to type in successive generations.

BRIEF SUMMARY OF THE INVENTION

The new Rhododendron has not been observed under all possible environmental conditions. The phenotype may vary somewhat with variations in environment such as temperature, daylength, light intensity, nutritional and water status without, however, any variance in genotype.

The following traits have been repeatedly observed and are determined to be the unique characteristics of 'Angelina'. These characteristics in combination distinguish 'Angelina' as a new and distinct cultivar:

1. Uniform, upright and outwardly spreading plant habit.
2. Dark green foliage.
3. Numerous showy double hose-in-hose white-colored flowers.
4. Long flowering period; plants stay in flower for about 30 days.

Plants of the new Rhododendron can be compared to plants of the single-flowered cultivar 'Aline', not patented. However, in side-by-side comparisons conducted in Lochristi, Belgium, plants of the new Rhododendron are more vigorous, have more uniform branching habit, and have longer lasting flowers than plants of the cultivar 'Aline'.

BRIEF DESCRIPTION OF THE PHOTOGRAPHS

The accompanying colored photographs illustrate the overall appearance of the new Rhododendron, showing the colors as true as it is reasonably possible to obtain in colored reproductions of this type. Colors in the photographs may differ slightly from the color values cited in the detailed botanical description, which accurately describe the colors of the new Rhododendron.

The photograph at the top of the sheet comprises a side perspective view of a typical plant of 'Angelina'.

The photograph at the bottom of the sheet is a close-up view of typical flowers of 'Angelina'. Plants in the photographs were about two years old.

DETAILED BOTANICAL DESCRIPTION

The aforementioned and following observations, measurements, values, and comparisons describe plants grown in Lochristi, Belgium, in an outdoor nursery in 17-cm containers under conditions which approximate commercial Rhododendron production conditions. Plants were grown for about 2 years with day temperatures averaging 18° C. and night temperatures averaging 10° C. Plants were pinched about 5 times during the production of these plants. In the following description, color references are made to The Royal Horticultural Society Colour Chart except where general terms of ordinary dictionary significance are used.

Botanical classification: *Rhododendron simsii* cultivar 'Angelina'.

Parentage:

*Male or pollen parent.*—Unidentified proprietary seedling selection of *Rhododendron simsii,* not patented.

*Female or seed parent.*—Unidentified proprietary seedling selection of *Rhododendron simsii,* not patented.

Propagation:

*Type.*—By terminal cuttings.

*Time to initiate roots.*—Summer: About 12 days at temepratures of 22° C. Winter: About 16 days at temperatures of 22° C.

*Time to develop roots.*—Summer: About 50 days at temperatures of 22° C. Winter: About 60 days at temperatures of 22° C.

*Root description.*—Fine and freely branching.

Plant description:

*Plant form and growth habit.*—Perennial, evergreen, upright and outwardly spreading, rounded, uniform plant habit. Vigorous growth habit. Appropriate for 12 to 17-cm containers.

*Branching habit.*—Pinching produces about two lateral branches; plants are typically pinched multiple times.

*Plant height, soil level to top of flowers.*—About 35 cm.

*Plant diameter, area of spread.*—About 30 cm.

*Lateral branch description.*—Length: About 5 to 6 cm. Diameter: About 2 mm. Internode length: About 1.5 to 2 cm. Texture: Slightly pubescent. Color: Immature: 144A. Mature, woody: 165A.

Foliage description:

*Arrangement.*—Alternate, single.

*Quantity of leaves per lateral branch.*—About 17.

*Length.*—About 5 to 7 cm.

*Width.*—About 2.5 to 3.8 cm.

*Shape.*—Elliptic.

*Apex.*—Obtuse.

*Base.*—Obtuse.

*Margin.*—Entire.

*Texture.*—Leathery; slightly pubescent on upper surface.

*Color.*—Young foliage, upper surface: 144A. Young foliage, lower surface: 144A. Mature foliage, upper surface: 139A; venation, 137A. Mature foliage, lower surface: 137B; venation, 146B.

*Petiole.*—Length: About 0.5 to 1 cm. Diameter: About 1 to 1.2 mm. Color: 137B.

Flower description:

*Natural flowering season.*—Early spring after sufficient cool period. Flower arrangement: Double hose-in-hose flowers arranged singly at terminals. Freely flowering; usually about 3 to 8 flowers and flower buds per lateral stem. Not fragrant.

*Flower longevity.*—Plants maintain good flower substance for about four weeks. Flowers persistent.

*Flowers.*—Depth: About 3.5 to 4 cm. Diameter: About 4 cm. Shape: Rounded.

*Flower bud.*—Length: About 1.5 cm. Diameter: About 1 cm. Shape: Conical. Color: White, close to 155D.

*Petals and sepals.*—Arrangement: In multiple whorls, at least 5 petals and about 5 sepals; fused at base. Shape: Spatulate with rounded apex. Margin: Entire with slightly undulating edge which gives a ruffled appearance. Length, outer whorl: About 4 to 5 cm. Width, outer whorl: About 4 to 5 cm. Texture: Smooth, satiny. Color: When opening, upper surface: 142B. When opening, lower surface: White, close to 155D. Fully opened, upper and lower surfaces: White, close to 155D. Petaloids: Irregular in shape and size, similar in color to petals and sepals.

*Peduncles.*—Length: About 1 to 2 cm. Angle: Erect. Strength: Flexible, strong. Color: 144A.

*Reproductive organs.*—Androecium: No stamens observed, all transformed into petal-like structures. Gynoecium: Quantity of pistils: One. Pistil length: About 2.5 mm. Stigma shape: Oval. Stigma color: White. Style length: About 2 mm. Style color: White. Ovary color: 49C. Seed: Seed production has not been observed.

Disease resistance: Resistance to known pathogens of Rhododendron has not been observed on plants grown under commercial conditions.

Temperature tolerance: Plants of the new Rhododendron tolerate temperatures from 0 to 35° C.

It is claimed:

1. A new and distinct Rhododendron plant named 'Angelina', as illustrated and described.

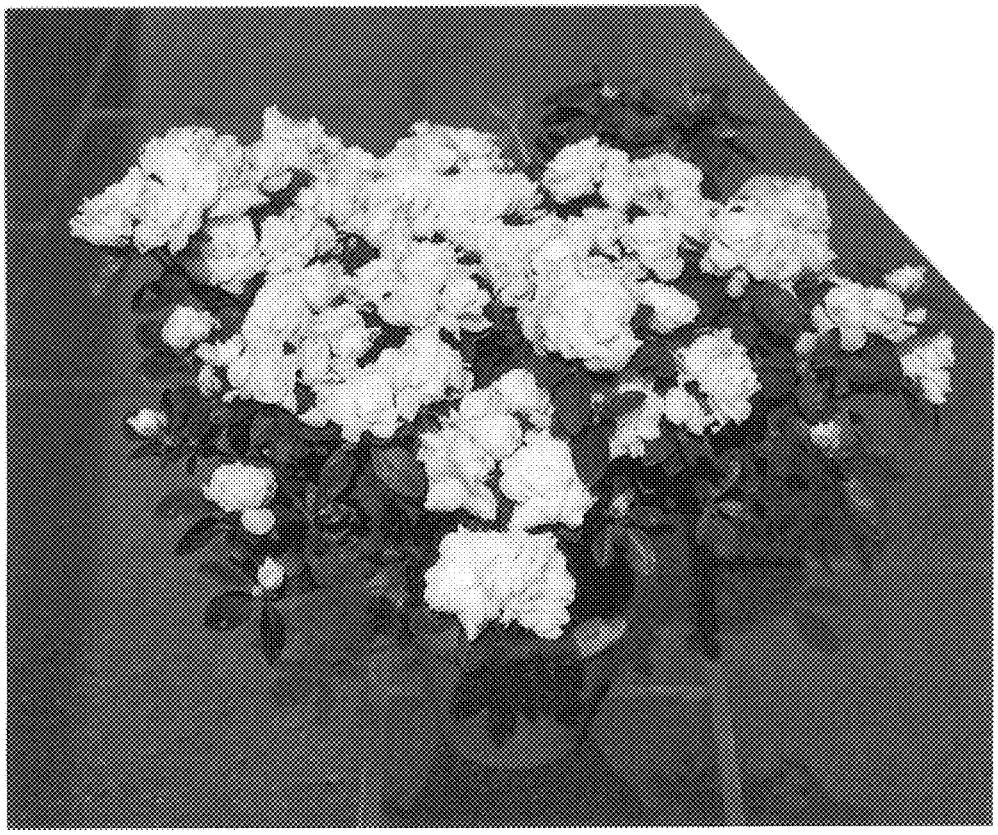
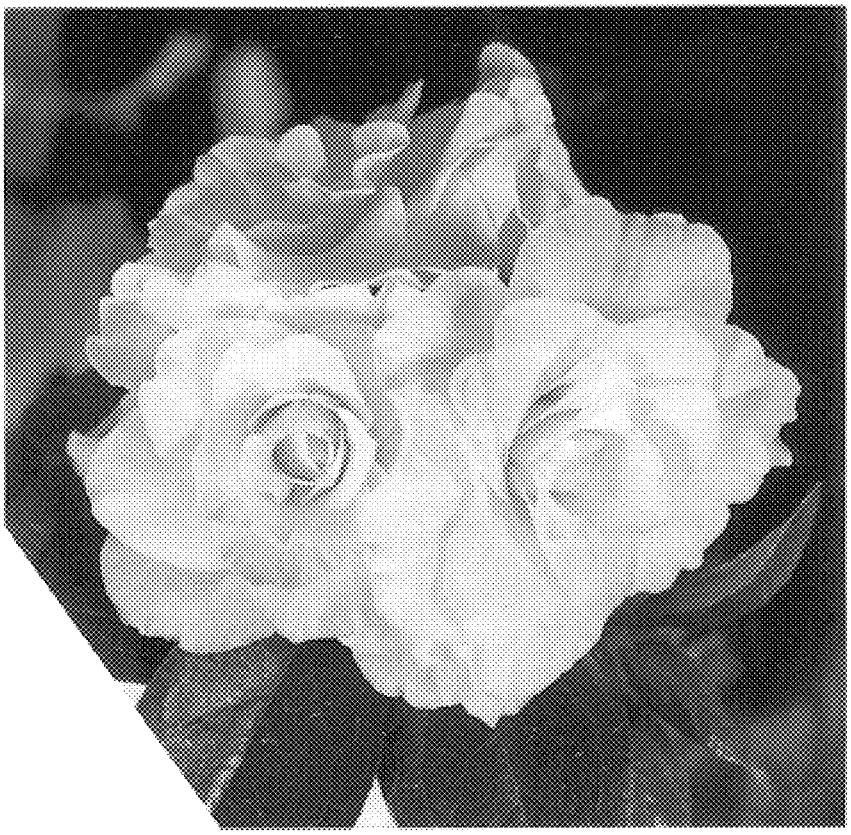

* * * * *